United States Patent
Boverman et al.

(10) Patent No.: US 10,357,178 B2
(45) Date of Patent: Jul. 23, 2019

(54) SYSTEM AND METHOD FOR ENHANCED ELECTRICAL IMPEDANCE TOMOGRAPHY

(71) Applicant: General Electric Company, Schenectady, NY (US)

(72) Inventors: Gregory Boverman, Saratoga Springs, NY (US); David Michael Davenport, Niskayuna, NY (US); Jeffrey Michael Ashe, Gloversville, NY (US); Bruce Courtney Campbell Amm, Clifton Park, NY (US)

(73) Assignee: General Electric Company, Schenectady, NY (US)

( * ) Notice: Subject to any disclaimer, the term of this patent is extended or adjusted under 35 U.S.C. 154(b) by 414 days.

(21) Appl. No.: 14/970,589

(22) Filed: Dec. 16, 2015

(65) Prior Publication Data

US 2017/0172451 A1 Jun. 22, 2017

(51) Int. Cl.
*A61B 5/053* (2006.01)
*G06T 11/00* (2006.01)
*A61B 5/00* (2006.01)

(52) U.S. Cl.
CPC .......... *A61B 5/0536* (2013.01); *A61B 5/7221* (2013.01); *G06T 11/003* (2013.01); *A61B 2576/00* (2013.01)

(58) Field of Classification Search
CPC ..... A61B 5/0536; A61B 5/7221; A61B 5/743; G06T 11/003
USPC ....................................................... 600/547
See application file for complete search history.

(56) References Cited

U.S. PATENT DOCUMENTS

| | | |
|---|---|---|
| 6,007,532 A | 12/1999 | Netherly |
| 8,755,873 B2 | 6/2014 | Sunderland |
| 8,868,205 B2 | 10/2014 | Ross et al. |
| 8,990,040 B2 | 3/2015 | Ross |
| 2006/0085048 A1 | 4/2006 | Cory et al. |
| 2011/0295096 A1 | 12/2011 | Bibian et al. |
| 2012/0232810 A1 | 9/2012 | Kaipio et al. |
| 2013/0109962 A1 | 5/2013 | Uutela |
| 2013/0184606 A1* | 7/2013 | Ginor .................. A61B 5/0536 600/547 |
| 2013/0217993 A1 | 8/2013 | Brunner et al. |

(Continued)

OTHER PUBLICATIONS

Loan, "Generalizing the singular value decomposition", SIAM Journal on Numerical Analysis, vol. 13, Issue 1, pp. 76-83, 1976.

(Continued)

*Primary Examiner* — Daniel L Cerioni (57) ABSTRACT

A method includes applying a plurality of currents to a plurality of electrodes disposed on a surface surrounding an anatomical region in a subject. Further, the method includes measuring a plurality of voltages generated in response to the plurality of currents. The method also includes selecting a coarse-scale basis corresponding to a response function associated with the plurality of electrodes. Moreover, the method includes determining simultaneously an internal admittivity corresponding to the anatomical region and a contact impedance corresponding to the plurality of electrodes based on the plurality of voltages and the coarse-scale basis. The method also includes reconstructing the diagnostic image based on the internal admittivity.

9 Claims, 6 Drawing Sheets

(56) References Cited

U.S. PATENT DOCUMENTS

2013/0307566 A1* 11/2013 Malone ............... A61B 5/7235
324/649

OTHER PUBLICATIONS

Golub et al., Generalized cross-validation as a method for choosing a good ridge parameter, Technometrics, vol. 21, Issue 2, pp. 215-223, 1979.

Isaacson, Distinguishability of conductivities by electric current computed tomography, IEEE Trans. Med Imag., vol. MI-5, pp. 91-95, 1986.

Cheng et al., "Electrode models for electric current computed tomography", IEEE Trans. Biomed. Eng, vol. 36, Issue 9, pp. 918-924, 1989.

Somersalo et al., "Existence and uniqueness for electrodemodels for electric current computed tomography", SIAM Journal on Applied Mathematics, vol. 52, Issue 4, pp. 1023-1040, 1992.

Hua et al., "Using compound electrodes in electrical impedance tomography", Biomedical Engineering IEEE Transactions on , vol. 40, Issue 1, pp. 29-34, 1993.

Hua et al., "Finite element modeling of electrode-skin contact impedance in electrical impedance tomography", Biomedical Engineering, IEEE Transactions on, vol. 40,Issue 4, pp. 335-343, 1993.

Vauhkonen et al., "Three-dimensional electrical impedance tomography based on the complete electrode model", IEEE Trans. Biomed. Eng, vol. 46, Issue 9, pp. 1150-1160, 1999.

Vauhkonen et al., "A MATLAB package for the EIDORS project to reconstruct two-dimensional EIT images", Physiological Measurement, vol. 22, Issue 1, pp. 107-111, 2001.

Kim et al., The complete electrode model for EIT in a mammography geometry, Physiological Measurement, vol. 28, Issue 7, pp. S57-S69, 2007.

Boverman et al., "Methods for Compensating for Variable Electrode Contact in EIT", IEEE Transactions On Biomedical Engineering, vol. 56, Issue 12, pp. 2762-2771, Dec. 2009.

Liu et al., "Estimation of conductivity changes in a region Of interest with electrical impedance Tomography", Computational Physics (physics.comp-ph); Medical Physics (physics.med-ph), pp. 1-19, Mar. 26, 2014.

* cited by examiner

SYSTEM AND METHOD FOR ENHANCED ELECTRICAL IMPEDANCE TOMOGRAPHY

BACKGROUND

Embodiments of the present specification relate generally to Electrical Impedance Tomography, and more particularly to systems and methods for simultaneous image reconstruction and estimation of time-varying electrode contact impedances in Electrical Impedance Tomography.

Electrical Impedance Tomography (EIT) is a non-invasive imaging tool with applications in numerous fields such as medicine, geophysics, environmental sciences, and nondestructive testing of materials. In recent years, EIT has being increasingly used in medical applications such as detection of pulmonary emboli, monitoring of apnea, monitoring of heart function and blood flow, and breast cancer detection. Also, some examples of non-medical applications of EIT include locating underground mineral deposits, detection of leaks in underground storage tanks, detection of corrosion and small defects such as cracks or voids in metals.

Typically, use of the EIT technique for imaging entails positioning a plurality of electrodes on the skin around an anatomical region in a subject being examined. Further, a low voltage alternating electrical current is applied to one or more electrodes. A resulting potential difference is measured between each pair of electrodes among the plurality of electrodes. An image of impedance within the body is generated based on the measured potential differences. Techniques such as parallel data collection and noise reduction have enabled EIT systems to provide clinically useful images of dynamic phenomena.

One significant problem with EIT is that the quality of each electrode's contact with the body varies significantly over time. Specifically, occurrence of electrochemical processes results in significant variations in the impedance of the skin-electrode boundary over time. Additionally, any motion by the subject being imaged may also result in variations in the impedance of the skin-electrode boundary over time. Some currently available EIT techniques attempt to maximize sensitivity to changes in conductivity and permittivity within the anatomical region by applying currents to all the electrodes. Certain other techniques entail use of compound electrodes. However, use of the compound electrodes calls for non-standard electrode designs and system configurations, thereby resulting in increased cost of the EIT system.

BRIEF DESCRIPTION

In accordance with one aspect of the present specification, a method is presented. The method includes applying a plurality of currents to a plurality of electrodes disposed on a surface surrounding an anatomical region in a subject. Furthermore, the method includes measuring a plurality of voltages generated in response to the plurality of currents. The method also includes selecting a coarse-scale basis corresponding to a response function associated with the plurality of electrodes. In addition, the method further includes determining simultaneously an internal admittivity corresponding to the anatomical region and a contact impedance corresponding to the plurality of voltages and the coarse-scale basis. Moreover, the method also includes reconstructing a diagnostic image based on the internal admittivity.

In accordance with another aspect of the present specification, a system is presented. The system includes a signal transceiver unit communicatively coupled to a plurality of electrodes disposed on a surface surrounding an anatomical region in a subject. The signal transceiver is configured to apply a plurality of currents to the plurality of electrodes and measure a plurality of voltages from the plurality of electrodes in response to the applied plurality of currents. The system further includes a model generator unit communicatively coupled to the signal transceiver unit and configured to select a coarse-scale basis corresponding to a response function associated with the plurality of electrodes. The system also includes an image reconstruction unit communicatively coupled to the model generator unit and configured to receive the plurality of voltages, determine simultaneously internal admittivity corresponding to the anatomical region and a contact impedance corresponding to the plurality of electrodes based on the plurality of voltages and the coarse-scale basis, and reconstruct a diagnostic image based on the internal admittivity.

In accordance with yet another aspect of the present specification, an electrical impedance tomography system is presented. The electrical impedance tomography system includes a plurality of electrodes disposed on a surface surrounding an anatomical region in a subject. The electrical impedance tomography system further includes a processing subsystem, where the processing subsystem includes a signal transceiver unit communicatively coupled to a plurality of electrodes disposed on a surface surrounding an anatomical region in a subject and configured to apply a plurality of currents to the plurality of electrodes and measure a plurality of voltages from the plurality of electrodes in response to the applied plurality of currents. The processing subsystem is further includes a model generator unit communicatively coupled to the signal transceiver unit and configured to select a coarse-scale basis corresponding to a response function associated with the plurality of electrodes. The processing subsystem also includes an image reconstruction unit communicatively coupled to the model generator unit and configured to receive the plurality of voltages, determine simultaneously an internal admittivity corresponding to the anatomical region and a contact impedance corresponding to the plurality of electrodes based on the plurality of voltages and the coarse-scale basis, and reconstruct a diagnostic image based on the internal admittivity. The system also includes a display communicatively coupled to the processing subsystem and configured to visualize at least the diagnostic image.

DRAWINGS

These and other features and aspects of embodiments of the present invention will become better understood when the following detailed description is read with reference to the accompanying drawings in which like characters represent like parts throughout the drawings, wherein.

DETAILED DESCRIPTION

As will be described in detail hereinafter, systems and methods are configured for enhanced quality of image reconstruction in Electrical Impedance Tomography. More particularly, the systems and methods are configured for simultaneous image reconstruction and estimation of time-varying electrode contact impedances in Electrical Impedance Tomography. As used herein, the terms "processor" and "computer" and related terms, e.g., "processing device", "computing device", and "controller" are not limited to just those integrated circuits referred to in the art as a computer, but broadly refers to a microcontroller, a microcomputer, a programmable logic controller (PLC), an application specific integrated circuit, and other programmable circuits, and these terms are used interchangeably herein. In the embodiments described herein, memory may include, but is not limited to, a computer-readable medium, such as a random access memory (RAM), and a computer-readable non-volatile medium, such as flash memory. Alternatively, a floppy disk, a compact disc read only memory (CD-ROM), a magneto-optical disk (MOD), and/or a digital versatile disc (DVD) may also be used. Also, in the embodiments described herein, additional input channels may be, but are not limited to, computer peripherals associated with an operator interface such as a mouse and a keyboard. Alternatively, other computer peripherals may also be used that may include, for example, but not be limited to, a scanner. Furthermore, in the exemplary embodiment, additional output channels may include, but not be limited to, an operator interface monitor.

Further, as used herein, the terms "software" and "firmware" are interchangeable, and include any computer program stored in memory for execution by personal computers, workstations, clients and servers. As used herein, the term "non-transitory computer-readable media" is intended to be representative of any tangible computer-based device implemented in any method or technology for short-term and long-term storage of information, such as, computer-readable instructions, data structures, program modules and sub-modules, or other data in any device. Therefore, the methods described herein may be encoded as executable instructions embodied in a tangible, non-transitory, computer readable medium, including, without limitation, a storage device and a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including, without limitation, volatile and nonvolatile media, and removable and non-removable media such as a firmware, physical and virtual storage, CD-ROMs, DVDs, and any other digital source such as a network or the Internet, as well as yet to be developed digital means, with the sole exception being a transitory, propagating signal.

The term 'diagnostic image' refers to a two dimensional (2D) image having pixel values representative of internal conductivities within a body part of a subject. The term 'diagnostic image' may also refer to a three dimensional (3D) image having voxel values representative of internal conductivities. The term 'electrical impedance' refers to a measure of resistance to flow of current in an electrical circuit when a voltage is applied. Electrical impedance in general is a complex quantity. The real part of the electrical impedance is referred to as resistance and the imaginary part is referred to as reactance. In general, the reactance includes an inductance and a capacitance, electrical properties of an inductor and a capacitor respectively. The term 'admittance' is used to refer to an inverse of the electrical impedance. Also, the term conductance is used to refer to an inverse of the resistance and the term 'susceptance' is used to refer to an inverse of the reactance. The term 'impeditivity' refers to an intrinsic property of a material representative of an impediment to the flow of current through the material. The impeditivity of a material is related to its electrical impedance. Similarly, the terms 'admittivity,' 'conductivity,' and 'susceptivity' are intrinsic properties of a material that are respectively related to 'admittance,' 'conductance,' and 'susceptance' of the material.

Figure 1:
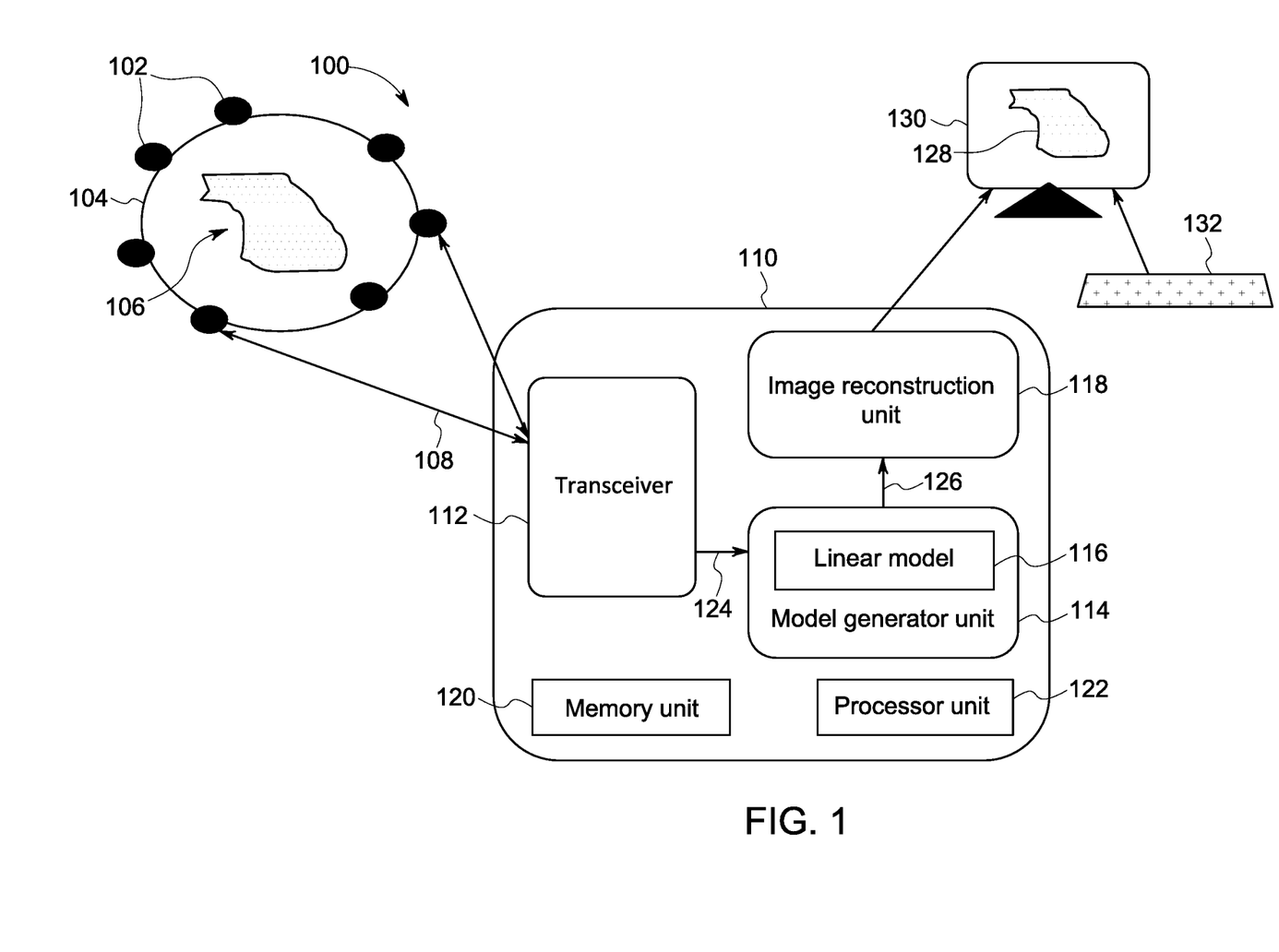
FIG. 1 illustrates a system for generating a diagnostic image, in accordance with aspects of present specification.

FIG. 1 illustrates an electrical impedance tomography (EIT) system 100 for enhanced electrical impedance tomography, in accordance with aspects of present specification. The EIT system 100 includes a plurality of electrodes 102. These electrodes may be disposed on an external surface 104 of a subject being imaged. In one example, the electrodes 102 may be disposed on the skin around an anatomical region 106 of the subject, such as a patient being imaged. The electrodes 102 are configured to apply a plurality of low voltage alternating currents to the external surface 104 of the subject. Additionally, the electrodes 102 are also configured to measure a plurality of voltages 108 that are generated in response to the applied of electrical currents. Alternatively, the electrodes 102 are configured to apply a plurality of voltages to the external surface 104 of the subject and measure a plurality of currents. In such an embodiment, reference numeral 108 may be representative of the plurality of currents.

The EIT system 100 also includes a processing subsystem 110 communicatively coupled to the electrodes 102 and configured to receive the voltages 108. The EIT system 100 and the processing subsystem 110 in particular is configured to generate an EIT image 128 of enhanced quality. In particular, the processing subsystem 110 generates the EIT image 128 by simultaneously estimating time-varying internal admittivity and time-varying electrode contact impedances based on the voltages 108. Moreover, the EIT system 100 also includes a display device 130 for displaying at least the enhanced EIT image 128. Further, the EIT system 100 also includes a user interface 132. The user interface 132 may be used to provide one or more parameters for use by the processing subsystem 110 or control displaying by the display device 130.

In a presently contemplated configuration, the processing subsystem 110 includes a signal transceiver unit 112, a model generator unit 114, and an image reconstruction unit 118. The processing subsystem 110 further includes a memory unit 120 and a processor unit 122. In addition, the processing subsystem 110 includes a communication bus (not shown) configured to communicatively couple one or more units 112, 114, 118, 120, and 122 in the processing subsystem 110. In one embodiment, the electrodes 102 may be communicatively coupled to signal transceiver unit 112 of the processing subsystem 110. Further, the display device 130 may be communicatively coupled to the image reconstruction unit 118.

The signal transceiver unit 112 includes components and circuitry required to aid the electrodes 102 in applying a plurality of current signals to the anatomical region 106. Also, the signal transceiver unit 112 is configured to receive the voltages 108 generated by the anatomical region 106 in response to the applied current signals. In one embodiment, the signal transceiver unit 112 is configured to simultaneously activate the electrodes 102 by applying a plurality of current signals (or a plurality of voltage signals) to the anatomical region 106. In some embodiments, the signal transceiver unit 112 is configured process the voltages 108 to generate a pre-processed signal 124. In one example, the signal transceiver unit 112 may process the voltages 108 via use of various processing steps such as filtering, digitization, normalization, and the like. The pre-processed signal 124 may be provided to the model generator unit 114.

The model generator unit 114 is communicatively coupled to the signal transceiver unit 112 and configured to determine an electrode model 126 based on the voltages 108. In one embodiment, the electrode model 126 is a Complete Electrode Model (CEM). Also, in some embodiments, reference numeral 126 may be representative of both the pre-processed signal 124 and a plurality of basis functions representative of the CEM. It may be noted that the CEM is based on a finite element model that entails use of hundreds of thousands to millions of triangular or tetrahedral elements. In one embodiment, the model generator unit 114 is configured to generate a fine-scale basis function corresponding to each element. In such an embodiment, a large number of basis functions are required to represent a response function associated with the electrodes 102.

In another embodiment, the model generator unit 114 is configured to generate a coarse-scale basis having a limited number of basis functions. In one embodiment, the coarse-scale basis corresponds to a finite subset of the fine-scale basis. Typically, the coarse-scale basis includes basis functions corresponding to non-adjacent elements in the finite element model. The model generator unit 114 is configured to determine the coarse-scale basis corresponding to a response function associated with the plurality of electrodes 102. Furthermore, the model generator unit 114 is configured to determine an internal admittivity representative of spatially varying admittivity across the external surface 104 based on the coarse-scale basis functions, the voltages 108, and the applied current signals. In one embodiment, the model generator unit 114 is configured to generate a finite dimensional linear operator based on the coarse-scale basis. Moreover, the model generator unit 114 may also be configured to determine the internal admittivity x(t) based on a matrix multiplication of the linear operator P with an admittivity solution p(t) in terms of the coarse-scale basis as indicated in equation (1).

$$x(t)=Pp(t) \quad (1)$$

where x(t) is an N×1 vector, P is an N×M matrix having M coarse-scale basis functions of an N-dimensional space, and p(t) is an admittivity solution corresponding to the coarse-scale basis corresponding to the linear operator P.

Figure 3:
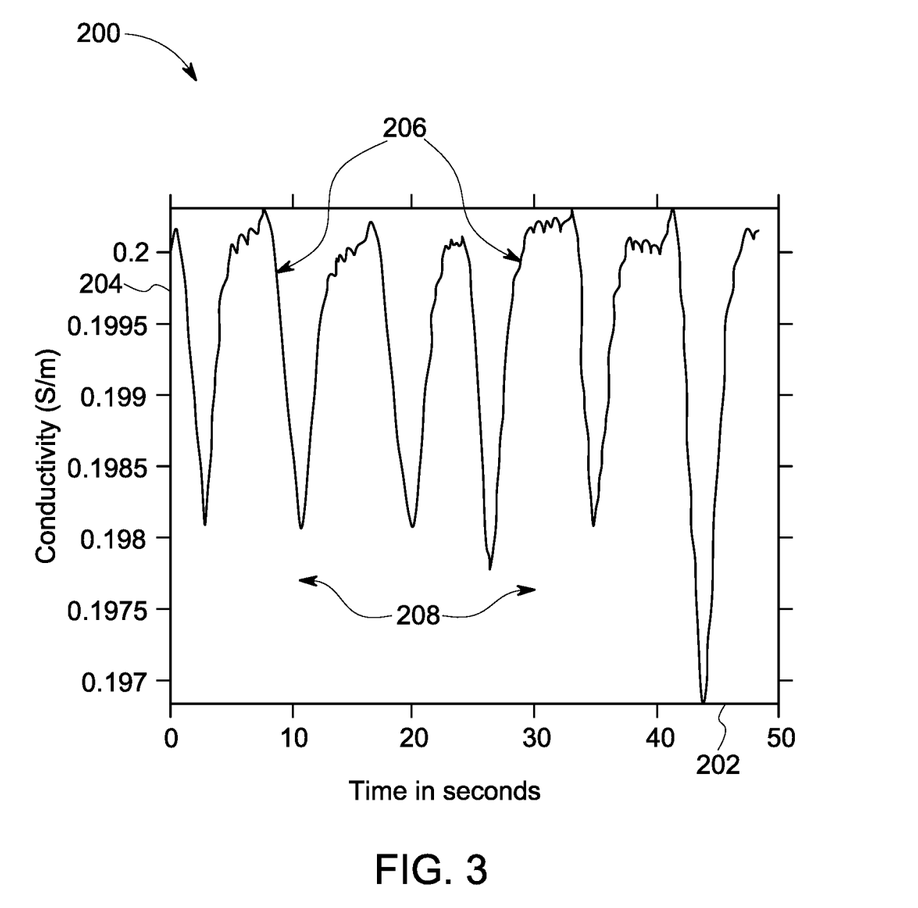
FIG. 3 is a graph illustrating time varying conductivity of an anatomical region in a patient, in accordance with aspects of present specification.

It may be noted that the admittivity p(t) is time-varying and an example function of a real part of the admittivity p(t) is illustrated in FIG. 3.

In one embodiment, a single coarse-scale basis function may be used in equation (1) to determine a global admittivity corresponding to the anatomical region 106. Also, in another embodiment, a plurality of coarse-scale basis functions may be used to determine the internal admittivity. In such an embodiment, each of the plurality of coarse-scale basis functions may represent one portion of the anatomical region 106. For example, if the anatomical region 106 includes two lobes of the lungs and the heart, a separate coarse-scale basis function may be used for each of the lung lobes and the heart.

The image reconstruction unit 118 is communicatively coupled to the model generator unit 114 and configured to receive the electrode model 126. The image reconstruction unit 118 is further configured to model the voltages 108 based on a linear measurement model 116. One example of the linear measurement model is presented in equation (2).

$$y(t)=J_y Pp(t)+J_z z(t)+y(0)+n(t) \quad (2)$$

In equation (2), P is a matrix of size N×M. M is a number of functions in the coarse-scale basis, p(t) is a M×1 column vector representing the solution in terms functions of the coarse-scale basis, $J_y$ is the Jacobian matrix with respect to the fine-scale basis, $J_z$ is the Jacobian matrix with respect to contact impedances of the plurality of electrodes, z(t) is a column vector of contact impedances, n(t) is a column vector of noise measurements. Also, the term y(t) is a measurement vector and the index t is representative of a time instant.

The image reconstruction unit 118 is further configured to determine an internal admittivity corresponding to the anatomical region 106 based on the electrode model 126 and the voltages 108. The image reconstruction unit 118 is also configured to determine a contact impedance of the electrodes 102 based on the measured voltages 108 and the coarse-scale basis. A least squares solution for the internal admittivity and the contact impedance may be obtained based on the linear measurement model of equation (2). One example of a least squares solution of the internal admittivity p(t) and the contact impedance z(t) are respectively presented in equations (3)-(4).

$$p(t)=(J_p^H N J_p)^{-1} J_p^H N(y(t)-y(0)) \quad (3)$$

and $$z(t)=(J_z^H J_z)^{-1} J_z^H (y(t)-y(0)-J_p p(t)) \quad (4)$$

where, $J_p=J_y P$ and NT, $(I-J_z(J_z^H J_z)^{-1} J_z^H)$.

Figure 4:
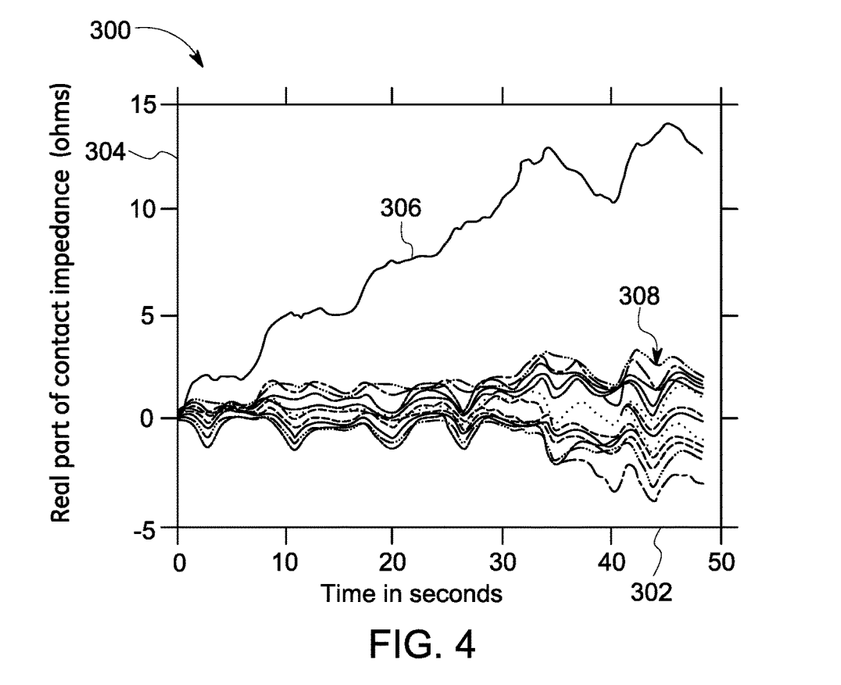
FIG. 4 is a graph illustrating a real part of contact impedance of electrodes, in accordance with aspects of present specification.
Figure 5:
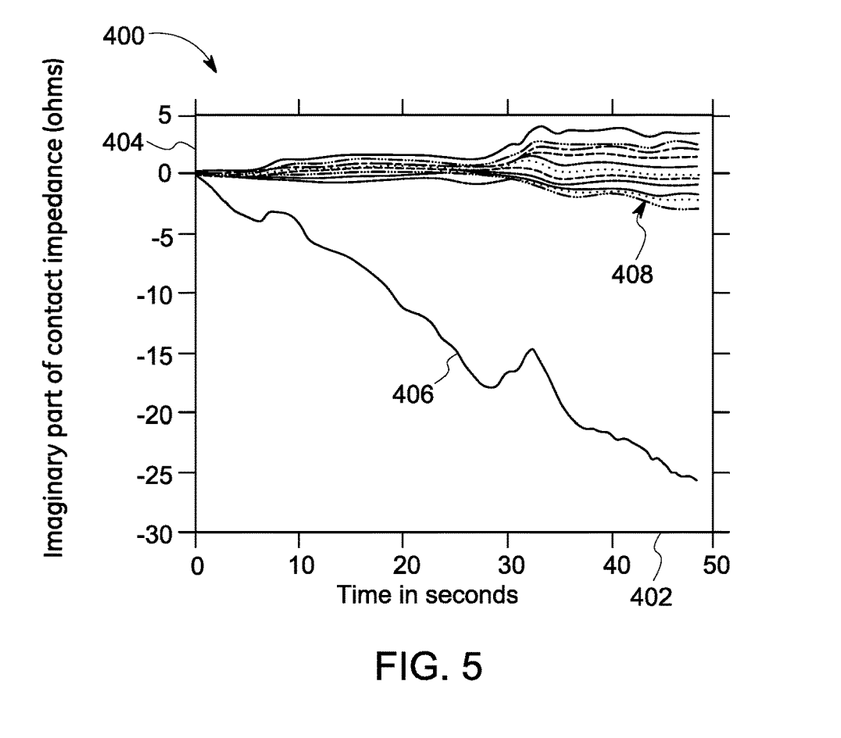
FIG. 5 is a graph illustrating an imaginary part of the contact impedance of electrodes, in accordance with aspects of the present specification.

It may be noted that one example of a real part and an imaginary part of the contact impedance is illustrated in FIGS. 4-5.

In one embodiment, the real part of the admittivity is determined based on equation (3) for each time instant. In another embodiment, the image reconstruction unit 118 is configured to simultaneously determine the internal admittivity and the contact impedance based on the complete electrode model (CEM) using an optimization technique. In such an embodiment, a parameter of the least squares solution is regularized for achieving a trade-off between minimizing the residual and minimizing the $l_2$ norm of the least squares solution. One example of a regularized simultaneous solution of the contact impedance and the internal admittivity is given by a regularized least squares solution depicted in equation (5).

$$\langle p(t), z(t) \rangle = \underset{p,z}{\operatorname{argmin}} \|y(t) - y(0) - J_P p(t) - J_z z(t)\| + \lambda^2 \|Lp(t)\|_2^2 \quad (5)$$

where $\lambda$ is a regularization parameter.

Equation (5) may be represented as a matrix system of equation as depicted in equation (6).

$$\begin{bmatrix} J_z & J_P \\ 0 & \lambda L \end{bmatrix} \begin{bmatrix} z(t) \\ p(t) \end{bmatrix} = \begin{bmatrix} y(t) - y(0) \\ 0 \end{bmatrix} \quad (6)$$

Also, in equation (6), L is a suitable Tikhonov matrix. In one embodiment, a value of the regularization parameter $\lambda$ is determined via use of a Generalized Cross-Validation technique (GCV technique). The GCV technique is based on a GCV function as indicated by equation (7).

$$V(\lambda) = \frac{1}{n} \frac{\|(I - A(\lambda))(y(t) - y(0))\|_2^2}{[1/n(\operatorname{Trace}(I - A(\lambda))]^2} \quad (7)$$

where A is representative of an influence matrix related to the matrix of equation (6).

Typically, use of cross validation techniques entails partitioning of data sets into complementary subsets, performing analysis on one subset, and validating the analysis on the other subset. While the cross validation technique provides a biased estimate of variance of the regularization parameter $\lambda$, the GCV technique provides an unbiased estimate of the variance of the regularization parameter $\lambda$. The regularization parameter $\lambda$ that minimizes equation (7) provides a regularization parameter $\lambda_{opt}$. The regularization parameter $\lambda_{opt}$ may be used to solve the matrix of equation (6). In one embodiment, the numerator of equation (7) is determined using a generalized singular value decomposition (GSVD) technique.

Further, the image reconstruction unit 118 is also configured to reconstruct a diagnostic image based on the determined internal admittivity. The internal admittivity solution p(t) obtained via use of equation (6) is used to determine the internal admittivity x(t) based on equation (1). In an embodiment where thirty two electrodes 102 are used, internal admittivity corresponding to thirty two electrode pairs may be determined. Moreover, the image reconstruction unit 118 reconstructs the diagnostic image 128 having one thousand and twenty four (1024) pixels arranged in thirty two rows and thirty two columns. Each pixel in the diagnostic image 128 has a value that is equal to the internal admittivity associated with a corresponding electrode pair. For example, a pixel corresponding to a third row and a fourth column may have a pixel value corresponding to an internal admittivity between the third and fourth electrodes among the thirty two electrodes. When the diagnostic image 128 is a time varying image, the pixel values may correspond to a difference value in the internal admittivity for a plurality of pairs of electrodes at successive time instants.

In one embodiment, the reconstruction unit 118 is also configured to determine a quality indicator for the diagnostic image 128 based on the contact impedance. The contact impedance of each of the plurality of electrodes 102 is compared with a quality threshold value and a quality of contact of the electrode 102 with the surface 104 is determined based on the comparison. If the quality of contact of the electrode 102 is not acceptable, the electrode 102 may be readjusted before acquiring new measurements. In one embodiment, when the poor contact of an electrode 102 contributes to image distortions, pixels of the image may be annotated with a quality indicator. In other embodiments, quality indicators corresponding to all the pixels may be annotated on the image. Also, in one example, the quality indicator may include a "good" quality indicator, a "bad" quality indicator, a "poor" quality indicator, and the like.

The processor unit 122 is communicatively coupled to the communication bus and may include at least one of an arithmetic logic unit, a microprocessor, a general purpose controller, and a processor array to perform the desired computations or run the computer programs. In one embodiment, the processor unit 122 may be configured to aid the signal transceiver unit 112, the model generator unit 114, and the image reconstruction unit 118 in performing associated tasks. It may be noted that while the embodiment of FIG. 1 depicts the processor unit 122 as a separate unit, in certain embodiments, the signal transceiver unit 112, the model generator unit 114, the image reconstruction unit 118 may include a corresponding processor unit.

In addition, the memory unit 120 is communicatively coupled to the communications bus and may be accessed by one or more of the processor unit 122, the signal transceiver unit 112, the model generator unit 114, and the image reconstruction unit 118. In an exemplary embodiment, the memory unit 120 may include one or more memory modules. The memory unit 120 may be a non-transitory storage medium. For example, the memory may be a dynamic random access memory (DRAM) device, a static random access memory (SRAM) device, flash memory or other memory devices. In one embodiment, the memory may include a non-volatile memory or similar permanent storage device, media such as a hard disk drive, a floppy disk drive, a compact disc read only memory (CD-ROM) device, a digital versatile disc read only memory (DVD-ROM) device, a digital versatile disc random access memory (DVD-RAM) device, a digital versatile disc rewritable (DVD-RW) device, a flash memory device, or other non-volatile storage devices. In another embodiment, a non-transitory computer readable medium may be encoded with a program having instructions to instruct the processor unit 122 to perform functions of the signal transceiver unit 112, the model generator unit 114, and the image reconstruction unit 118.

Figure 2:
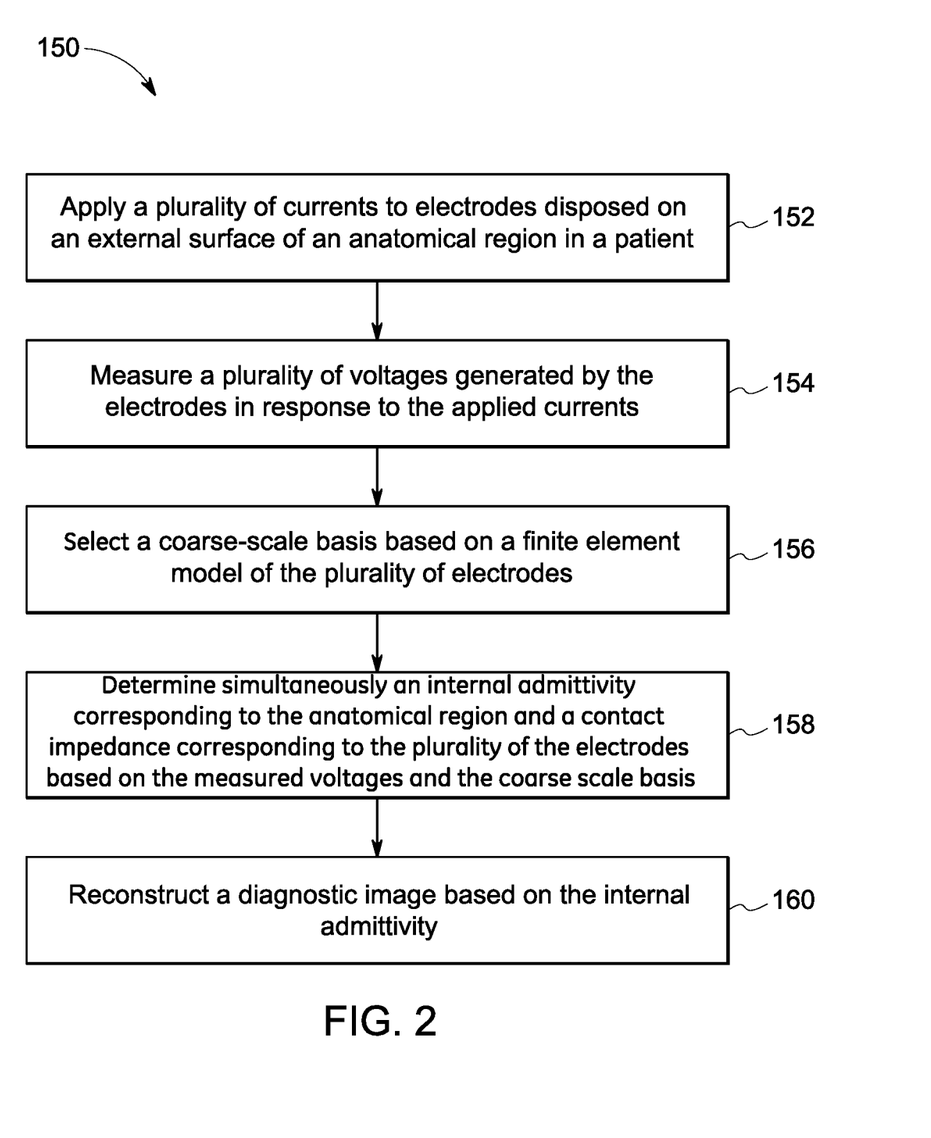
FIG. 2 is a flow chart illustrating a method for generating a diagnostic image, in accordance with aspects of present specification.

FIG. 2 is a flow chart 150 illustrating a method for generating a diagnostic image, in accordance with aspects of present specification. The method 150 may be described with reference to the components of FIG. 1. In one example, the method 150 is performed by the processing subsystem 110 of FIG. 1.

One or more electrodes 102 are disposed on the external surface 104 that surrounds the anatomical region 106 of the subject being imaged. At step 152, a plurality of currents is applied to electrodes 102. In one embodiment, the currents may be applied using a simple ring of thirty two standard ECG electrodes disposed around the circumference of the chest of the patient/subject. In one example, the electrodes 102 are excited by thirty two independent high output impedance current sources operating at a single modulation frequency of 10 kHz. Alternatively, voltages may be applied to the electrodes 102.

Subsequently, at step 154, a plurality of voltages 108 generated in response to applied currents may be measured. In one embodiment, the voltages 108 are measured at a frame rate of about nineteen frames per second. In another embodiment, the voltages 108 are measured using a matched filter detection technique. Further, the measured voltages 108 may be processed via use of analog to digital conversion. In some embodiments, a plurality of currents generated in response to the applied voltages may be measured. It may be noted that in certain embodiments, steps 152 and 154 may be performed by the signal transceiver unit 112 of FIG. 1.

Moreover, at step 156, a coarse-scale basis corresponding to a response function associated with the electrodes 102 is selected. In one embodiment, the model generator unit 114 may be employed to select the coarse-scale basis. Additionally, in one embodiment, the coarse-scale basis is chosen from a fine-scale basis by selecting a finite number of functions. The fine-scale basis, as previously noted, is a large collection of basis functions representative of a response surface corresponding to the plurality of electrodes. In one embodiment, the fine-scale basis is determined based on an electrode model. In one example, a complete electrode model (CEM) is used as the electrode model. A finite element mesh is determined for the CEM. The fine-scale basis corresponding to the finite element mesh includes hundreds of thousands of functions. In one embodiment, the coarse-scale basis is represented as a finite dimensional linear operator by stacking a finite number of basis functions in columns of a matrix. In one embodiment, the anatomical region 106 may encompass one or more organs of the patient. In such an embodiment where the anatomical region 106 includes distinctly identifiable portions, a plurality of coarse-scale basis functions corresponding to the distinctly identifiable portions of the anatomical region 106 is determined.

In addition, an internal admittivity corresponding to the anatomical region 106 and a contact impedance corresponding to the electrodes 102 may be simultaneously determined based on the measured voltages and the coarse-scale basis, as depicted by step 158. In one embodiment, the denominator of equation (7) is computed a priori for all possible candidate values of the regularization parameter $\lambda$. One embodiment of determining the regularization parameter $\lambda$ is presented with reference to FIGS. 6-7.

Moreover, at step 160, a diagnostic image, such as the diagnostic image 128 is reconstructed based on the internal admittivity determined at step 158. In one embodiment, the diagnostic image 128 having pixels representative of differential conductivity values is reconstructed based on the internal admittivity. The term 'differential conductivity value' refers to a difference between a conductivity value (real part of internal admittivity) determined at step 158 and a reference conductivity value. Steps 158-160 may be performed by the image reconstruction unit 118.

FIG. 3 is a graphical representation 200 illustrating time varying conductivity (for example, a real part of the admittivity) of an anatomical region in a patient, in accordance with aspects of present specification. The graph 200 includes an x-axis 202 representative of time in seconds and a y-axis 204 representative of differential conductivity in Siemens per meter. The graph 200 also includes a curve 206 representative of internal conductivity of the anatomical region. The differential conductivity is determined based on a reference frame corresponding to a previous time instant. The reference frame for generating the curve 206 corresponds to an end of an expiration phase of a breathing cycle of the patient. The curve 206 exhibits a plurality of valley regions 208 in the curve 206. These valley regions 208 correspond to a plurality of inspiration phases 208 of the breathing cycle of the patient. It may be noted that the curve 206 is obtained based on the linear measurement model for the plurality of voltages given by equation (2).

FIG. 4 is a graphical representation 300 illustrating a real part of contact impedance (i.e., resistance) of electrodes, such as the electrodes 102 of FIG. 1, in accordance with aspects of present specification. The graph 300 includes an x-axis 302 representative of time in seconds and a y-axis 304 representative of the resistance in Ohms. Curves 306, 308 are presented in the graphical representation 300. These curves 306, 308 are representative of resistance values corresponding to the electrodes 102. The curves 308 exhibit a small correlation with the respiration cycle of the patient with the resistance decreasing (increasing conductivity) during the inspiration phase and increasing (decreasing conductivity) during the expiration phase of the breathing cycle. It may be noted that the decrease in resistance during the expiration phase is consistent with the expansion of the chest during the inspiration phase, which in turn increases the pressure on the electrodes 102. The curve 306 corresponds to one of the plurality of electrodes 102 exhibiting a large resistance value. In one embodiment, the contact impedance is determined based on equation (4) for each time instant.

FIG. 5 is a graphical representation 400 illustrating an imaginary part of the contact impedance (i.e., reactance) of electrodes, such as the electrodes 102 of FIG. 1, in accordance with aspects of present specification. The graph 400 includes an x-axis 402 representative of time in seconds and a y-axis 404 representative of the reactance in Ohms. Curves 408, 406 correspond to the reactance of the electrodes 102. Also, the curves 408 exhibit variations which are not periodical and these variations may be attributed to at least one of electrochemical processes and movements of the patient. The curve 406 corresponds to one of the plurality of electrodes 102 exhibiting a large reactance value. In one embodiment, the contact impedance is determined based on equation (4) for each time instant.

Figure 6:
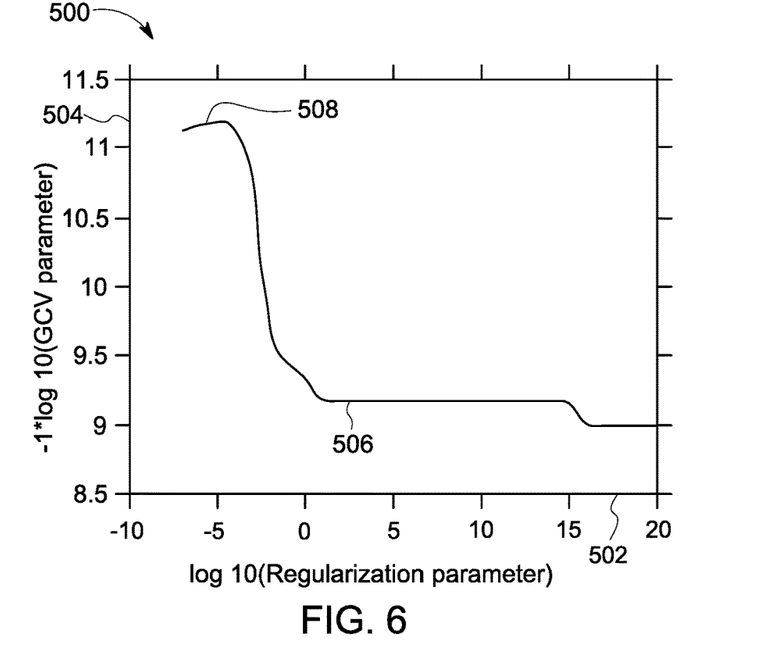
FIGS. 6-7 are graphs illustrating selection of a regularization parameter, in accordance with aspects of present specification.
Figure 7:
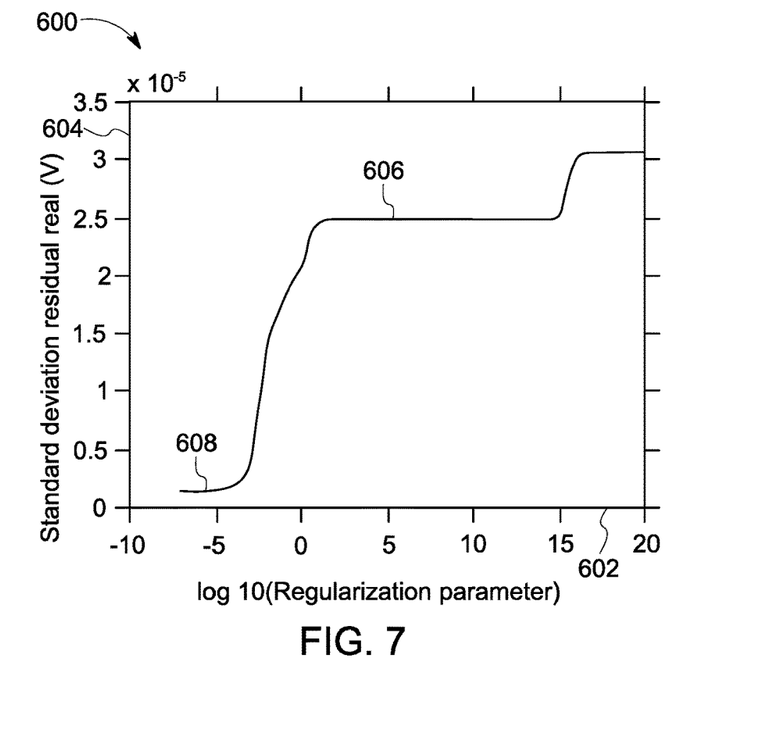

FIGS. 6-7 illustrate a method for selecting a value of a regularization parameter, in accordance with aspects of present specification. FIG. 6 is a graph 500 illustrating a generalized cross-validation function determined based on measurement data. The graph 500 includes an x-axis 502 representative of a regularization parameter value and a y-axis 504 representative of a GCV parameter. A plurality of conductivity values corresponding to a plurality of voltage values in a window of twenty seconds of the measurement data is determined using equation (6). A data point corresponding to a large change in the successive conductivity values is identified. Furthermore, a GCV function at the identified data point is determined for a plurality of regularization parameters based on the equation (7). Curve 506 is representative of the GCV function on a logarithmic scale. It may be observed that initial portion of the curve 506 has a maximum value 508.

FIG. 7 is a graph 600 illustrating a standard deviation of a residual determined based on measurement data. The graph 600 includes an x-axis 602 representative of a regularization parameter value and a y-axis 604 representative of standard deviation of the residual. A data point corresponding to a large change in the conductivity value within first twenty seconds of the measurement data is identified. A standard deviation of the residual is determined for a plurality of regularization parameters. Curve 606 is representative of the standard deviation of the residual on a logarithmic scale. It may be observed that initial portion of the curve 606 has a minimum value 608.

In one example, an optimum value of the regularization parameter is determined corresponding to the maximum value 508 and the minimum value 608 in FIG. 6 and FIG. 7 respectively. In another example, an optimum value of the regularization parameter may be identified along the curve 506 between the maximum value 508 and the plateau region of the curve 506. Similarly, an optimum value of the regularization parameter may be identified along the curve 606 between the minimum value 608 and the plateau region of the curve 606. In these examples, the optimum values may be identified based on experimentation or user input.

Figure 8:
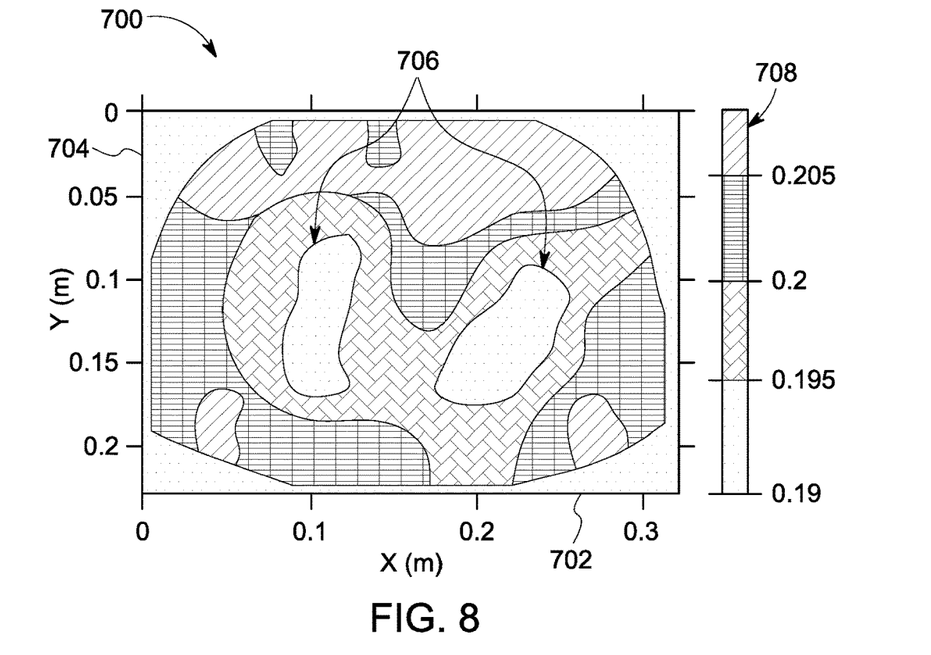
FIG. 8 depicts an image generated based on time varying contact impedances, in accordance with aspects of present specification.

FIG. 8 depicts an image 700 generated based on time varying contact impedances, in accordance with aspects of present specification. The image 700 has an x-axis 702 representative of a length in meters measured from left to right and a y-axis 704 representative of a length in meters measured from top to bottom. A grayscale bar 708 is representative of values of the pixels in the image 700. The image 700 is generated based on data collected during inspiration at 42.16 seconds after the start of the data collection when stable signals without transient components are available. The image 700 is generated by simultaneously estimating internal admittivity and the contact impedance. Specifically, the internal admittivity is obtained by solving equation (6) and reconstructing the pixel values of the image as a linear combination of the plurality of coarse-scale basis functions. In particular, the image 700 is generated based on magnitudes of the computed pixels. The magnitude of the pixels corresponds to a real part of the internal conductivity values. The magnitudes of the pixels are indicated by the grayscale bar 708. The regularization parameter value corresponding to a residual standard deviation of 15 microvolts is used in generating the image 700. The example image 700 of FIG. 7 is generally representative of the lungs in a patient. It may be observed that two lobes of the lungs 706 are clearly discernible in the image 700. It may be noted that the lung regions have lower conductivity during the inspiration phase of the breathing cycle. The pixels corresponding to the two lobes of the lungs 706 have low values as the image 700 corresponds to the inspiration phase of the respiratory cycle.

Figure 9:
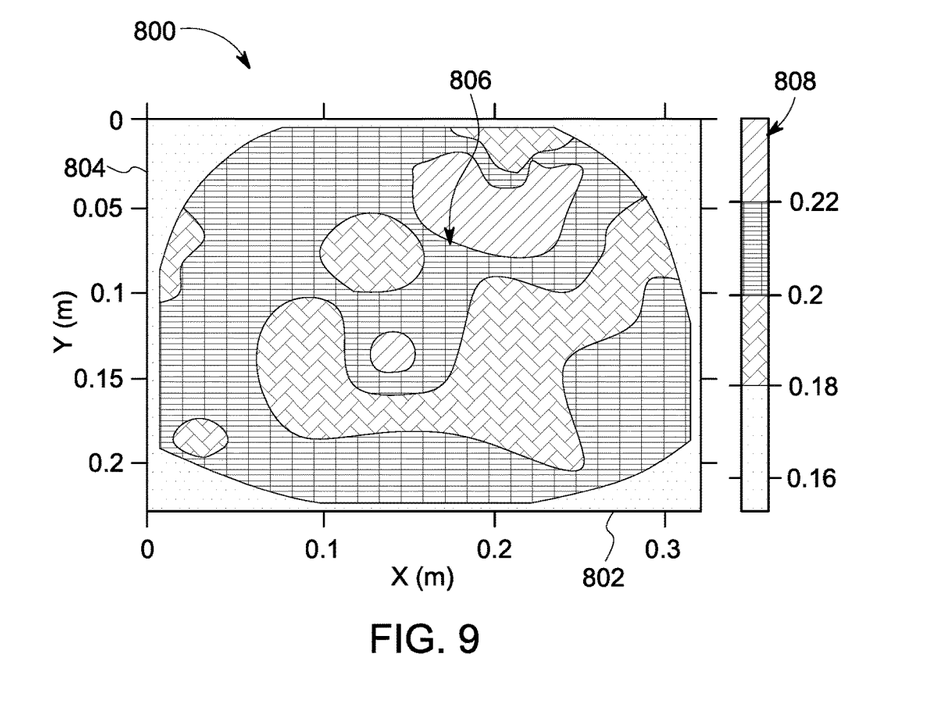
FIG. 9 depicts a an image generated based on constant contact impedances, in accordance with aspects of present specification.

FIG. 9 depicts an image 800 generated based on constant contact impedances, in accordance with aspects of present specification. The image 800 has an x-axis 802 representative of a length in meters measured from left to right and a y-axis 804 representative of a length in meters measured from top to bottom. A grayscale bar 808 is representative of values of the pixels in the image 800. The image 800 is generated based on data collected at 42.16 seconds after the start of the data collection when stable signals without transient components are available. The image 800 is generated by independently estimating internal admittivity and assuming a constant contact impedance. Specifically, the internal admittivity is obtained by solving the equation (3) and reconstructing the pixel values of the image as a linear combination of the coarse-basis functions. The image 800 is generated based on magnitudes of the computed pixels. The regularization parameter value corresponding to a residual standard deviation of 15 microvolts is used in generating the image 800. The example image 800 of FIG. 8 is generally representative of the lungs in a patient. It may be observed that two lobes of the lungs are not clearly visible in the image 800. The image 700 of FIG. 7 generated based on simultaneously estimated internal admittivity and contact impedance is superior in quality when compared to the image 800 generated based only on estimated internal admittivity.

Various embodiments of systems and methods for generating an image described hereinabove using an EIT system facilitate measurement of admittivity variations within an anatomical region with high sensitivity. Furthermore, the simultaneous estimation of the contact impedance of the plurality of electrodes configured to measure voltages and time varying internal admittivity of an anatomical region in the patient based on the measured voltages aids in overcoming image artifacts due to variations of contact impedance and improving the quality of the generated diagnostic image. Furthermore, the systems and methods provide numerically stable solutions when compared to solutions provided by conventional techniques.

It is to be understood that not necessarily all such objects or advantages described above may be achieved in accordance with any particular embodiment. Thus, for example, those skilled in the art will recognize that the systems and techniques described herein may be embodied or carried out in a manner that achieves or improves one advantage or group of advantages as taught herein without necessarily achieving other objects or advantages as may be taught or suggested herein.

While the technology has been described in detail in connection with only a limited number of embodiments, it should be readily understood that the specification is not limited to such disclosed embodiments. Rather, the technology can be modified to incorporate any number of variations, alterations, substitutions or equivalent arrangements not heretofore described, but which are commensurate with the spirit and scope of the claims. Additionally, while various embodiments of the technology have been described, it is to be understood that aspects of the specification may include only some of the described embodiments. Accordingly, the specification is not to be seen as limited by the foregoing description, but is only limited by the scope of the appended claims.

The invention claimed is:

1. A system, comprising:
   a signal transceiver unit communicatively coupled to a plurality of electrodes disposed on a surface surrounding an anatomical region in a subject and configured to:
   apply a plurality of currents to the plurality of electrodes;
   measure a plurality of voltages from the plurality of electrodes in response to the applied plurality of currents;
   a model generator unit communicatively coupled to the signal transceiver unit and configured to select a coarse-scale basis corresponding to a response function associated with the plurality of electrodes;
   an image reconstruction unit communicatively coupled to the model generator unit and configured to:
   receive the plurality of voltages;
   model the plurality of voltages using a linear measurement model, wherein the linear measurement model is based on an internal admittivity corresponding to the anatomical region and a contact impedance corresponding to the plurality of electrodes;
   determine, using an optimization technique, simultaneously both the internal admittivity corresponding to the anatomical region and the contact impedance corresponding to the plurality of electrodes based on the plurality of voltages, the coarse-scale basis, and the linear measurement model;
   reconstruct a diagnostic image based on the internal admittivity;
   annotate the diagnostic image by a quality indicator, wherein the quality indicator is determined based on the contact impedance; and
   display the diagnostic image on a display.

2. The system of claim 1, wherein the image reconstruction unit is further configured to determine the internal admittivity based on a least squares solution corresponding to the linear measurement model or a regularized least squares solution corresponding to the linear measurement model.

3. The system of claim 2, wherein the image reconstruction unit is configured to determine a regularization parameter.

4. The system of claim 3, wherein the image reconstruction unit is configured to determine the regularization parameter via use of a generalized cross-validation technique.

5. The system of claim 1, wherein the model generator unit is configured to generate a complete electrode model corresponding to the plurality of electrodes.

6. The system of claim 5, wherein the model generator unit is further configured to generate a finite element mesh corresponding to the complete electrode model.

7. The system of claim 1, wherein the model generator unit is further configured to generate a finite dimensional linear operator.

8. The system of claim 1, wherein the image reconstruction unit is further configured to determine a quality indicator for each pixel in the diagnostic image based on the contact impedance.

9. An electrical impedance tomography system, comprising:
   a plurality of electrodes disposed on a surface surrounding an anatomical region in a subject;
   a processing subsystem comprising:
      a signal transceiver unit communicatively coupled to the plurality of electrodes disposed on a surface surrounding an anatomical region in a subject and configured to:
         apply a plurality of currents to the plurality of electrodes;
         measure a plurality of voltages from the plurality of electrodes in response to the applied plurality of currents;
      a model generator unit communicatively coupled to the signal transceiver unit and configured to select a coarse-scale basis corresponding to a response function associated with the plurality of electrodes;
      an image reconstruction unit communicatively coupled to the model generator unit and configured to:
         receive the plurality of voltages;
         model the plurality of voltages using a linear measurement model, wherein the linear measurement model is based on an internal admittivity corresponding to the anatomical region and a contact impedance corresponding to the plurality of electrodes;
         determine, using an optimization technique, simultaneously both the internal admittivity corresponding to the anatomical region and the contact impedance corresponding to the plurality of electrodes based on the plurality of voltages the coarse-scale basis, and the linear measurement model;
         reconstruct a diagnostic image based on the internal admittivity;
         annotate the diagnostic image by a quality indicator, wherein the quality indicator is determined based on the contact impedance; and
      a display communicatively coupled to the processing subsystem and configured to visualize at least the diagnostic image.

* * * * *